US007981123B2

(12) United States Patent
Séguin

(10) Patent No.: US 7,981,123 B2
(45) Date of Patent: Jul. 19, 2011

(54) SURGICAL DEVICE FOR CONNECTING SOFT TISSUE

(75) Inventor: Jacques Séguin, Paris (FR)

(73) Assignee: Evalve, Inc., Redwood City, CA (US)

( * ) Notice: Subject to any disclaimer, the term of this patent is extended or adjusted under 35 U.S.C. 154(b) by 0 days.

(21) Appl. No.: 12/699,768

(22) Filed: Feb. 3, 2010

(65) Prior Publication Data

US 2010/0191256 A1 Jul. 29, 2010

Related U.S. Application Data

(60) Continuation of application No. 11/354,612, filed on Feb. 14, 2006, now Pat. No. 7,682,369, which is a continuation of application No. 10/877,279, filed on Jun. 24, 2004, now Pat. No. 7,288,097, which is a division of application No. 10/202,599, filed on Jul. 24, 2002, now Pat. No. 6,770,083, which is a division of application No. 09/523,018, filed on Mar. 10, 2000, now Pat. No. 6,461,366, which is a continuation of application No. PCT/FR98/01960, filed on Sep. 12, 1997.

(51) Int. Cl.
*A61B 17/00* (2006.01)
(52) U.S. Cl. ........................................ 606/142
(58) Field of Classification Search .............. 606/16, 606/37, 42, 139, 142–144, 148, 151, 157, 606/185; 600/17, 37; 623/2.1–2.37, 3.1, 623/3.16, 3.21
See application file for complete search history.

(56) References Cited

U.S. PATENT DOCUMENTS

| 2,108,206 A | 2/1938 | Meeker |
| 3,296,668 A | 1/1967 | Aiken |
| 3,378,010 A | 4/1968 | Codling |
| 3,557,780 A | 1/1971 | Sato |
| 3,671,979 A | 6/1972 | Moulopoulos |
| 3,874,388 A | 4/1975 | King et al. |
| 4,007,743 A | 2/1977 | Blake |

(Continued)

FOREIGN PATENT DOCUMENTS

DE 3504292 * 7/1986

(Continued)

OTHER PUBLICATIONS

Abe et al., "De Vega's annuloplasty for acquired tricuspid disease: Early and late results in 110 patients" Ann. Thorac. Surg. (1989) 48:670-676.

(Continued)

*Primary Examiner* — Kevin T Truong
(74) *Attorney, Agent, or Firm* — Sughrue Mion, PLLC; Jonathan Feuchtwang

(57) ABSTRACT

The invention comprises a surgical instrument including an external tube (2) and two elongated members (4) positioned in said tube (2), each of which includes a distal end (10*a*) for capturing one of the two tissue zones (M1, M2) to be attached. The instrument (1) may further comprise a catching member (22, 25) for each tissue (M1, M2) to be attached; a rod (15, 16) linked to each catching member (22, 25) enabling tension to move axially, said rod (15, 16) being separable from said catching member (22, 25) when a tension is exerted on it beyond a certain threshold; and a member (17*a*) forming a stop for locking axially each catching member (22, 25) during said tension.

7 Claims, 4 Drawing Sheets

U.S. PATENT DOCUMENTS

| | | |
|---|---|---|
| 4,056,854 A | 11/1977 | Boretos et al. |
| 4,064,881 A | 12/1977 | Meredith |
| 4,112,951 A | 9/1978 | Hulka et al. |
| 4,235,238 A | 11/1980 | Ogiu et al. |
| 4,297,749 A | 11/1981 | Davis et al. |
| 4,425,908 A | 1/1984 | Simon |
| 4,458,682 A | 7/1984 | Cerwin |
| 4,484,579 A | 11/1984 | Meno et al. |
| 4,487,205 A | 12/1984 | Di Giovanni et al. |
| 4,498,476 A | 2/1985 | Cerwin et al. |
| 4,510,934 A | 4/1985 | Batra |
| 4,531,522 A | 7/1985 | Bedi et al. |
| 4,578,061 A | 3/1986 | Lemelson |
| 4,641,366 A | 2/1987 | Yokoyama et al. |
| 4,686,965 A | 8/1987 | Bonnet et al. |
| 4,777,951 A | 10/1988 | Cribier et al. |
| 4,809,695 A | 3/1989 | Gwathmey et al. |
| 4,917,089 A | 4/1990 | Sideris |
| 4,944,295 A | 7/1990 | Gwathmey et al. |
| 4,969,890 A | 11/1990 | Sugita et al. |
| 4,994,077 A | 2/1991 | Dobben |
| 5,015,249 A | 5/1991 | Nakao et al. |
| 5,019,096 A | 5/1991 | Fox, Jr. et al. |
| 5,042,707 A | 8/1991 | Taheri |
| 5,047,041 A | 9/1991 | Samuels |
| 5,049,153 A | 9/1991 | Nakao et al. |
| 5,061,277 A | 10/1991 | Carpentier et al. |
| 5,069,679 A | 12/1991 | Taheri |
| 5,108,368 A | 4/1992 | Hammerslag et al. |
| 5,125,758 A | 6/1992 | DeWan |
| 5,171,252 A | 12/1992 | Friedland |
| 5,171,259 A | 12/1992 | Inoue |
| 5,190,554 A | 3/1993 | Coddington et al. |
| 5,195,968 A | 3/1993 | Lundquist et al. |
| 5,209,756 A | 5/1993 | Seedhom et al. |
| 5,226,429 A | 7/1993 | Kuzmak |
| 5,226,911 A | 7/1993 | Chee et al. |
| 5,234,437 A | 8/1993 | Sepetka |
| 5,242,456 A | 9/1993 | Nash et al. |
| 5,250,071 A | 10/1993 | Palermo |
| 5,251,611 A | 10/1993 | Zehel et al. |
| 5,254,130 A | 10/1993 | Poncet et al. |
| 5,261,916 A | 11/1993 | Engelson |
| 5,271,381 A | 12/1993 | Ailinger et al. |
| 5,275,578 A | 1/1994 | Adams |
| 5,282,845 A | 2/1994 | Bush et al. |
| 5,304,131 A | 4/1994 | Paskar |
| 5,306,283 A | 4/1994 | Conners |
| 5,306,286 A | 4/1994 | Stack et al. |
| 5,312,415 A | 5/1994 | Palermo |
| 5,314,424 A | 5/1994 | Nicholas |
| 5,318,525 A | 6/1994 | West et al. |
| 5,320,632 A | 6/1994 | Heidmueller |
| 5,325,845 A | 7/1994 | Adair |
| 5,330,442 A | 7/1994 | Green et al. |
| 5,332,402 A | 7/1994 | Teitelbaum |
| 5,350,397 A | 9/1994 | Palermo et al. |
| 5,350,399 A | 9/1994 | Erlebacher et al. |
| 5,359,994 A | 11/1994 | Krauter et al. |
| 5,368,564 A | 11/1994 | Savage |
| 5,368,601 A | 11/1994 | Sauer et al. |
| 5,383,886 A | 1/1995 | Kensey et al. |
| 5,403,312 A | 4/1995 | Yates et al. |
| 5,403,326 A | 4/1995 | Harrison et al. |
| 5,411,552 A | 5/1995 | Andersen et al. |
| 5,417,699 A | 5/1995 | Klein et al. |
| 5,417,700 A | 5/1995 | Egan |
| 5,423,857 A | 6/1995 | Rosenman et al. |
| 5,423,858 A | 6/1995 | Bolanos et al. |
| 5,423,882 A | 6/1995 | Jackman et al. |
| 5,431,666 A | 7/1995 | Sauer et al. |
| 5,437,551 A | 8/1995 | Chalifoux |
| 5,437,681 A | 8/1995 | Meade et al. |
| 5,447,966 A | 9/1995 | Hermes et al. |
| 5,450,860 A | 9/1995 | O'Connor |
| 5,456,400 A | 10/1995 | Shichman et al. |
| 5,456,684 A | 10/1995 | Schmidt et al. |
| 5,462,527 A | 10/1995 | Stevens-Wright et al. |
| 5,472,044 A | 12/1995 | Hall et al. |
| 5,476,470 A | 12/1995 | Fitzgibbons, Jr. |
| 5,477,856 A | 12/1995 | Lundquist |
| 5,478,309 A | 12/1995 | Sweezer et al. |
| 5,478,353 A | 12/1995 | Yoon |
| 5,487,746 A | 1/1996 | Yu et al. |
| 5,507,725 A | 4/1996 | Savage et al. |
| 5,507,757 A | 4/1996 | Sauer et al. |
| 5,520,701 A | 5/1996 | Lerch |
| 5,522,873 A | 6/1996 | Jackman et al. |
| 5,527,313 A | 6/1996 | Scott et al. |
| 5,527,321 A | 6/1996 | Hinchliffe |
| 5,527,322 A | 6/1996 | Klein et al. |
| 5,536,251 A | 7/1996 | Evard et al. |
| 5,540,705 A | 7/1996 | Meade et al. |
| 5,542,949 A | 8/1996 | Yoon |
| 5,554,185 A | 9/1996 | Block et al. |
| 5,569,274 A | 10/1996 | Rapacki et al. |
| 5,571,085 A | 11/1996 | Accisano, III |
| 5,571,137 A | 11/1996 | Marlow et al. |
| 5,571,215 A | 11/1996 | Sterman et al. |
| 5,575,802 A | 11/1996 | McQuilkin et al. |
| 5,582,611 A | 12/1996 | Tsuruta et al. |
| 5,593,424 A | 1/1997 | Northrup III |
| 5,593,435 A | 1/1997 | Carpentier et al. |
| 5,609,598 A | 3/1997 | Laufer et al. |
| 5,618,306 A | 4/1997 | Roth et al. |
| 5,620,452 A | 4/1997 | Yoon |
| 5,626,588 A | 5/1997 | Sauer et al. |
| 5,634,932 A | 6/1997 | Schmidt |
| 5,636,634 A | 6/1997 | Kordis et al. |
| 5,639,277 A | 6/1997 | Mariant et al. |
| 5,640,955 A | 6/1997 | Ockuly et al. |
| 5,649,937 A | 7/1997 | Bito et al. |
| 5,662,681 A | 9/1997 | Nash et al. |
| 5,669,917 A | 9/1997 | Sauer et al. |
| 2,097,018 A | 10/1997 | Chamberlain |
| 5,690,671 A | 11/1997 | McGurk et al. |
| 5,695,504 A | 12/1997 | Gifford, III et al. |
| 5,695,505 A | 12/1997 | Yoon |
| 5,702,825 A | 12/1997 | Keita et al. |
| 5,706,824 A | 1/1998 | Whittier |
| 5,709,707 A | 1/1998 | Lock et al. |
| 5,713,910 A | 2/1998 | Gordon et al. |
| 5,713,911 A | 2/1998 | Racenet et al. |
| 5,715,817 A | 2/1998 | Stevens-Wright et al. |
| 5,716,367 A | 2/1998 | Koike et al. |
| 5,718,725 A | 2/1998 | Sterman et al. |
| 5,719,725 A | 2/1998 | Nakao |
| 5,722,421 A | 3/1998 | Francese et al. |
| 5,725,542 A | 3/1998 | Yoon |
| 5,725,556 A | 3/1998 | Moser et al. |
| 5,738,649 A | 4/1998 | Macoviak |
| 5,741,280 A | 4/1998 | Fleenor |
| 5,749,828 A | 5/1998 | Solomon et al. |
| 5,769,812 A | 6/1998 | Stevens et al. |
| 5,769,863 A | 6/1998 | Garrison |
| 5,772,578 A | 6/1998 | Heimberger et al. |
| 5,782,845 A | 7/1998 | Shewchuk |
| 5,797,927 A | 8/1998 | Yoon |
| 5,797,960 A | 8/1998 | Stevens et al. |
| 5,810,847 A | 9/1998 | Laufer et al. |
| 5,810,849 A | 9/1998 | Kontos |
| 5,810,853 A | 9/1998 | Yoon |
| 5,810,876 A | 9/1998 | Kelleher |
| 5,814,029 A | 9/1998 | Hassett |
| 5,820,592 A | 10/1998 | Hammerslag |
| 5,820,631 A | 10/1998 | Nobles |
| 5,823,955 A | 10/1998 | Kuck et al. |
| 5,823,956 A | 10/1998 | Roth et al. |
| 5,824,065 A | 10/1998 | Gross |
| 5,827,237 A | 10/1998 | Macoviak et al. |
| 5,829,447 A | 11/1998 | Stevens et al. |
| 5,833,671 A | 11/1998 | Macoviak et al. |
| 5,836,955 A | 11/1998 | Buelna et al. |
| 5,840,081 A | 11/1998 | Andersen et al. |
| 5,843,031 A | 12/1998 | Hermann et al. |
| 5,849,019 A | 12/1998 | Yoon |
| 5,853,422 A | 12/1998 | Huebsch et al. |

| | | | | | |
|---|---|---|---|---|---|
| 5,855,271 A | 1/1999 | Eubanks et al. | 6,402,781 B1 | 6/2002 | Langberg et al. |
| 5,855,614 A | 1/1999 | Stevens et al. | 6,406,420 B1 | 6/2002 | McCarthy et al. |
| 5,860,990 A | 1/1999 | Nobles et al. | 6,419,669 B1 | 7/2002 | Frazier et al. |
| 5,868,733 A | 2/1999 | Ockuly et al. | 6,461,366 B1 | 10/2002 | Seguin |
| 5,876,399 A | 3/1999 | Chia et al. | 6,464,707 B1 | 10/2002 | Bjerken |
| 5,879,307 A | 3/1999 | Chio et al. | 6,482,224 B1 | 11/2002 | Michler et al. |
| 5,885,271 A | 3/1999 | Hamilton et al. | 6,485,489 B2 | 11/2002 | Teirstein et al. |
| 5,891,160 A | 4/1999 | Williamson, IV et al. | 6,508,828 B1 | 1/2003 | Akerfeldt et al. |
| 5,916,147 A | 6/1999 | Boury | 6,533,796 B1 | 3/2003 | Sauer et al. |
| 5,928,224 A | 7/1999 | Laufer | 6,537,314 B2 | 3/2003 | Langberg et al. |
| 5,944,733 A | 8/1999 | Engelson | 6,540,755 B2 | 4/2003 | Ockuly et al. |
| 5,947,363 A | 9/1999 | Bolduc et al. | 6,551,331 B2 | 4/2003 | Nobles et al. |
| 5,954,732 A | 9/1999 | Hart et al. | 6,562,037 B2 | 5/2003 | Paton et al. |
| 5,957,949 A | 9/1999 | Leonhard et al. | 6,562,052 B2 | 5/2003 | Nobles et al. |
| 5,972,020 A | 10/1999 | Carpentier et al. | 6,575,971 B2 | 6/2003 | Hauck et al. |
| 5,972,030 A | 10/1999 | Garrison et al. | 6,585,761 B2 | 7/2003 | Taheri |
| 5,980,455 A | 11/1999 | Daniel et al. | 6,599,311 B1 | 7/2003 | Biggs et al. |
| 5,989,284 A | 11/1999 | Laufer | 6,616,684 B1 | 9/2003 | Vidlund et al. |
| 6,015,417 A | 1/2000 | Reynolds, Jr. | 6,619,291 B2 | 9/2003 | Hlavka et al. |
| 6,019,722 A | 2/2000 | Spence et al. | 6,626,899 B2 | 9/2003 | Houser et al. |
| 6,022,360 A | 2/2000 | Reimels et al. | 6,626,930 B1 | 9/2003 | Allen et al. |
| 6,033,378 A | 3/2000 | Lundquist et al. | 6,629,534 B1 | 10/2003 | Dell et al. |
| 6,036,699 A | 3/2000 | Andreas et al. | 6,641,592 B1 | 11/2003 | Sauer et al. |
| 6,048,351 A | 4/2000 | Gordon et al. | 6,656,221 B2 | 12/2003 | Taylor et al. |
| 6,056,769 A | 5/2000 | Epstein et al. | 6,669,687 B1 | 12/2003 | Saadat |
| 6,059,757 A | 5/2000 | Macoviak et al. | 6,685,648 B2 | 2/2004 | Flaherty et al. |
| 6,060,628 A | 5/2000 | Aoyama et al. | 6,689,164 B1 | 2/2004 | Seguin |
| 6,060,629 A | 5/2000 | Pham et al. | 6,695,866 B1 | 2/2004 | Kuehn et al. |
| 6,063,106 A | 5/2000 | Gibson | 6,701,929 B2 | 3/2004 | Hussein |
| 6,066,146 A | 5/2000 | Carroll et al. | 6,702,825 B2 | 3/2004 | Frazier et al. |
| 6,068,628 A | 5/2000 | Fanton et al. | 6,702,826 B2 | 3/2004 | Liddicoat et al. |
| 6,068,629 A | 5/2000 | Haissaguerre et al. | 6,709,382 B1 | 3/2004 | Horner |
| 6,077,214 A | 6/2000 | Mortier et al. | 6,709,456 B2 | 3/2004 | Langberg et al. |
| 6,086,600 A | 7/2000 | Kortenbach | 6,718,985 B2 | 4/2004 | Hlavka et al. |
| 6,088,889 A | 7/2000 | Luther et al. | 6,719,767 B1 | 4/2004 | Kimblad |
| 6,099,505 A | 8/2000 | Ryan et al. | 6,723,038 B1 | 4/2004 | Schroeder et al. |
| 6,099,553 A | 8/2000 | Hart et al. | 6,726,716 B2 | 4/2004 | Marquez |
| 6,110,145 A | 8/2000 | Macoviak | 6,740,107 B2 | 5/2004 | Loeb et al. |
| 6,117,144 A | 9/2000 | Nobles et al. | 6,746,471 B2 | 6/2004 | Mortier et al. |
| 6,117,159 A | 9/2000 | Huebsch et al. | 6,752,813 B2 | 6/2004 | Goldfarb et al. |
| 6,123,699 A | 9/2000 | Webster, Jr. | 6,755,777 B2 | 6/2004 | Schweich et al. |
| 6,126,658 A | 10/2000 | Baker | 6,764,510 B2 | 7/2004 | Vidlund et al. |
| 6,132,447 A | 10/2000 | Dorsey | 6,767,349 B2 | 7/2004 | Ouchi |
| 6,136,010 A | 10/2000 | Modesitt et al. | 6,770,083 B2 | 8/2004 | Seguin |
| 6,143,024 A | 11/2000 | Campbell et al. | 6,797,001 B2 | 9/2004 | Mathis et al. |
| 6,159,240 A | 12/2000 | Sparer et al. | 6,797,002 B2 | 9/2004 | Spence et al. |
| 6,162,233 A | 12/2000 | Williamson, IV et al. | 6,860,179 B2 | 3/2005 | Hopper et al. |
| 6,165,164 A | 12/2000 | Hill et al. | 6,875,224 B2 | 4/2005 | Grimes |
| 6,165,183 A | 12/2000 | Kuehn et al. | 6,926,715 B1 | 8/2005 | Hauck et al. |
| 6,165,204 A | 12/2000 | Levinson et al. | 6,945,978 B1 | 9/2005 | Hyde |
| 6,168,614 B1 | 1/2001 | Andersen et al. | 6,949,122 B2 | 9/2005 | Adams et al. |
| 6,171,320 B1 | 1/2001 | Monassevitch | 6,966,914 B2 | 11/2005 | Abe |
| 6,182,664 B1 | 2/2001 | Cosgrove | 6,986,775 B2 | 1/2006 | Morales et al. |
| 6,187,003 B1 | 2/2001 | Buysse et al. | 7,004,970 B2 | 2/2006 | Cauthen III et al. |
| 6,190,408 B1 | 2/2001 | Melvin | 7,011,669 B2 | 3/2006 | Kimblad |
| 6,203,531 B1 | 3/2001 | Ockuly et al. | 7,048,754 B2 | 5/2006 | Martin et al. |
| 6,203,553 B1 | 3/2001 | Robertson et al. | 7,112,207 B2 | 9/2006 | Allen et al. |
| 6,206,893 B1 | 3/2001 | Klein et al. | 7,226,467 B2 | 6/2007 | Lucatero et al. |
| 6,206,907 B1 | 3/2001 | Marino et al. | 7,288,097 B2 | 10/2007 | Séguin |
| 6,210,419 B1 | 4/2001 | Mayenberger et al. | 7,341,584 B1 * | 3/2008 | Starkey ..................... 606/37 |
| 6,210,432 B1 | 4/2001 | Solem et al. | 7,381,210 B2 | 6/2008 | Zarbatany et al. |
| 6,245,079 B1 | 6/2001 | Nobles et al. | 7,464,712 B2 | 12/2008 | Oz et al. |
| 6,267,746 B1 | 7/2001 | Bumbalough | 7,497,822 B1 | 3/2009 | Kugler et al. |
| 6,267,781 B1 | 7/2001 | Tu | 7,533,790 B1 | 5/2009 | Knodel et al. |
| 6,269,819 B1 | 8/2001 | Oz et al. | 7,563,267 B2 | 7/2009 | Goldfarb et al. |
| 6,277,555 B1 | 8/2001 | Duran et al. | 7,563,273 B2 | 7/2009 | Goldfarb et al. |
| 6,283,127 B1 | 9/2001 | Sterman et al. | 7,604,646 B2 | 10/2009 | Goldfarb et al. |
| 6,283,962 B1 | 9/2001 | Tu et al. | 7,608,091 B2 | 10/2009 | Goldfarb et al. |
| 6,299,637 B1 | 10/2001 | Shaolian et al. | 7,635,329 B2 | 12/2009 | Goldfarb et al. |
| 6,306,133 B1 | 10/2001 | Tu et al. | 7,635,386 B1 * | 12/2009 | Gammie ................. 623/2.11 |
| 6,312,447 B1 | 11/2001 | Grimes | 7,651,502 B2 | 1/2010 | Jackson |
| 6,319,250 B1 | 11/2001 | Falwell et al. | 7,682,319 B2 | 3/2010 | Martin et al. |
| 6,322,559 B1 | 11/2001 | Daulton et al. | 7,682,369 B2 | 3/2010 | Séguin |
| 6,332,893 B1 | 12/2001 | Mortier et al. | 2001/0004715 A1 | 6/2001 | Duran et al. |
| 6,352,708 B1 | 3/2002 | Duran et al. | 2001/0005787 A1 | 6/2001 | Oz et al. |
| 6,355,030 B1 | 3/2002 | Aldrich et al. | 2001/0010005 A1 | 7/2001 | Kammerer et al. |
| 6,358,277 B1 | 3/2002 | Duran | 2001/0018611 A1 | 8/2001 | Solem et al. |
| 6,368,326 B1 | 4/2002 | Dakin et al. | 2001/0022872 A1 | 9/2001 | Marui |
| 6,402,780 B2 | 6/2002 | Williamson et al. | 2001/0037084 A1 | 11/2001 | Nardeo |

| | | |
|---|---|---|
| 2001/0039411 A1 | 11/2001 | Johansson et al. |
| 2001/0044568 A1 | 11/2001 | Langberg et al. |
| 2002/0013571 A1 | 1/2002 | Goldfarb et al. |
| 2002/0022848 A1 | 2/2002 | Garrison et al. |
| 2002/0026233 A1 | 2/2002 | Shaknovich |
| 2002/0035361 A1 | 3/2002 | Houser et al. |
| 2002/0035381 A1 | 3/2002 | Bardy et al. |
| 2002/0042651 A1 | 4/2002 | Liddicoat et al. |
| 2002/0055774 A1 | 5/2002 | Liddicoat |
| 2002/0055775 A1 | 5/2002 | Carpentier et al. |
| 2002/0058910 A1 | 5/2002 | Hermann |
| 2002/0058995 A1 | 5/2002 | Stevens |
| 2002/0077687 A1 | 6/2002 | Ahn |
| 2002/0087148 A1 | 7/2002 | Brock et al. |
| 2002/0087169 A1 | 7/2002 | Brock et al. |
| 2002/0087173 A1 | 7/2002 | Alferness et al. |
| 2002/0103532 A1 | 8/2002 | Langberg et al. |
| 2002/0107534 A1 | 8/2002 | Schaefer et al. |
| 2002/0147456 A1 | 10/2002 | Diduch et al. |
| 2002/0156526 A1 | 10/2002 | Hilavka et al. |
| 2002/0158528 A1 | 10/2002 | Tsuzaki et al. |
| 2002/0161378 A1 | 10/2002 | Downing |
| 2002/0169360 A1 | 11/2002 | Taylor et al. |
| 2002/0183766 A1 | 12/2002 | Seguin |
| 2002/0183835 A1 | 12/2002 | Taylor et al. |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |
| 2003/0074012 A1 | 4/2003 | Nguyen et al. |
| 2003/0078654 A1 | 4/2003 | Taylor et al. |
| 2003/0083742 A1 | 5/2003 | Spence et al. |
| 2003/0105519 A1 | 6/2003 | Fasol et al. |
| 2003/0105520 A1 | 6/2003 | Alferness et al. |
| 2003/0120340 A1 | 6/2003 | Lisk et al. |
| 2003/0120341 A1 | 6/2003 | Shennib et al. |
| 2003/0130669 A1 | 7/2003 | Damarati |
| 2003/0130730 A1 | 7/2003 | Cohn et al. |
| 2003/0144697 A1 | 7/2003 | Mathis et al. |
| 2003/0167071 A1 | 9/2003 | Martin et al. |
| 2003/0171776 A1 | 9/2003 | Adams et al. |
| 2003/0187467 A1 | 10/2003 | Schreck |
| 2003/0195562 A1 | 10/2003 | Collier et al. |
| 2003/0208231 A1 | 11/2003 | Williamson, IV et al. |
| 2003/0229395 A1 | 12/2003 | Cox |
| 2003/0233038 A1 | 12/2003 | Hassett |
| 2004/0002719 A1 | 1/2004 | Oz et al. |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049211 A1 | 3/2004 | Tremulis et al. |
| 2004/0073302 A1 | 4/2004 | Rourke et al. |
| 2004/0078053 A1 | 4/2004 | Berg et al. |
| 2004/0088047 A1 | 5/2004 | Spence et al. |
| 2004/0092962 A1 | 5/2004 | Thornton et al. |
| 2004/0097878 A1 | 5/2004 | Anderson et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |
| 2004/0122448 A1 | 6/2004 | Levine |
| 2004/0127981 A1 | 7/2004 | Rahdert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133082 A1 | 7/2004 | Abraham-Fuchs et al. |
| 2004/0133192 A1 | 7/2004 | Houser et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0138745 A1 | 7/2004 | Macoviak et al. |
| 2004/0148021 A1 | 7/2004 | Cartledge et al. |
| 2004/0152847 A1 | 8/2004 | Emri et al. |
| 2004/0152947 A1 | 8/2004 | Schroeder et al. |
| 2004/0153144 A1 | 8/2004 | Seguin |
| 2004/0158123 A1 | 8/2004 | Jayaraman |
| 2004/0162610 A1 | 8/2004 | Laiska et al. |
| 2004/0167539 A1 | 8/2004 | Kuehn et al. |
| 2004/0186486 A1 | 9/2004 | Roue et al. |
| 2004/0186566 A1 | 9/2004 | Hindrichs et al. |
| 2004/0193191 A1 | 9/2004 | Starksen et al. |
| 2004/0215339 A1 | 10/2004 | Drasler et al. |
| 2004/0220593 A1 | 11/2004 | Greenhalgh |
| 2004/0220657 A1 | 11/2004 | Nieminen |
| 2004/0225300 A1 | 11/2004 | Goldfarb et al. |
| 2004/0236354 A1 | 11/2004 | Seguin |
| 2004/0243229 A1 | 12/2004 | Vidlund et al. |
| 2004/0249452 A1 | 12/2004 | Adams et al. |
| 2004/0249453 A1 | 12/2004 | Cartledge et al. |
| 2005/0004583 A1 | 1/2005 | Oz et al. |
| 2005/0004665 A1 | 1/2005 | Aklog |
| 2005/0004668 A1 | 1/2005 | Aklog et al. |
| 2005/0021056 A1 | 1/2005 | St. Goar et al. |
| 2005/0021057 A1 | 1/2005 | St. Goar et al. |
| 2005/0021058 A1 | 1/2005 | Negro |
| 2005/0033446 A1 | 2/2005 | Deem et al. |
| 2005/0038508 A1 | 2/2005 | Gabbay |
| 2005/0049698 A1 | 3/2005 | Bolling et al. |
| 2005/0055089 A1 | 3/2005 | Macoviak et al. |
| 2005/0059351 A1 | 3/2005 | Cauwels et al. |
| 2005/0149014 A1 | 7/2005 | Hauck et al. |
| 2005/0159810 A1 | 7/2005 | Filsoufi |
| 2005/0197694 A1 | 9/2005 | Pai et al. |
| 2005/0197695 A1 | 9/2005 | Stacchino et al. |
| 2005/0216039 A1 | 9/2005 | Lederman |
| 2005/0228422 A1 | 10/2005 | Machold et al. |
| 2005/0228495 A1 | 10/2005 | Macoviak |
| 2005/0251001 A1 | 11/2005 | Hassett |
| 2005/0267493 A1 | 12/2005 | Schreck et al. |
| 2005/0273160 A1 | 12/2005 | Lashinski et al. |
| 2005/0287493 A1 | 12/2005 | Novak et al. |
| 2006/0004247 A1 | 1/2006 | Kute et al. |
| 2006/0015003 A1 | 1/2006 | Moaddes et al. |
| 2006/0030866 A1 | 2/2006 | Schreck |
| 2006/0030867 A1 | 2/2006 | Zadno |
| 2006/0030885 A1 | 2/2006 | Hyde |
| 2006/0058871 A1 | 3/2006 | Zakay et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0089671 A1 | 4/2006 | Goldfarb et al. |
| 2006/0089711 A1 | 4/2006 | Dolan |
| 2006/0184203 A1 | 8/2006 | Martin et al. |
| 2006/0195012 A1 | 8/2006 | Mortier et al. |
| 2006/0229708 A1 | 10/2006 | Powell et al. |
| 2006/0252984 A1 | 11/2006 | Rahdert et al. |
| 2007/0038293 A1* | 2/2007 | St.Goar et al. |
| 2007/0100356 A1* | 5/2007 | Lucatero et al. |
| 2007/0118155 A1* | 5/2007 | Goldfarb et al. |
| 2007/0129737 A1* | 6/2007 | Goldfarb et al. |
| 2007/0198082 A1* | 8/2007 | Kapadia et al. |
| 2008/0039935 A1* | 2/2008 | Buch et al. |
| 2008/0051703 A1* | 2/2008 | Thornton et al. |
| 2008/0051807 A1* | 2/2008 | St. Goar et al. |
| 2008/0097489 A1* | 4/2008 | Goldfarb et al. |
| 2008/0167714 A1* | 7/2008 | St. Goar et al. |
| 2008/0183194 A1* | 7/2008 | Goldfarb et al. |
| 2009/0163934 A1* | 6/2009 | Raschdorf, Jr. et al. |
| 2009/0177266 A1* | 7/2009 | Powell et al. |
| 2009/0198322 A1* | 8/2009 | Deem et al. |
| 2009/0270858 A1* | 10/2009 | Hauck et al. |
| 2009/0326567 A1* | 12/2009 | Goldfarb et al. |
| 2010/0016958 A1* | 1/2010 | St. Goar et al. |
| 2010/0022823 A1* | 1/2010 | Goldfarb et al. |

FOREIGN PATENT DOCUMENTS

| | | | |
|---|---|---|---|
| EP | 0 179 562 A1 | * | 4/1986 |
| EP | 0 179 562 B1 | * | 7/1989 |
| EP | 0 558 031 | * | 2/1993 |
| EP | 0 684 012 | * | 11/1995 |
| EP | 0 727 239 | * | 8/1996 |

| | | | |
|---|---|---|---|
| EP | 1 674 040 | * | 6/2006 |
| FR | 2768324 | * | 3/1999 |
| GB | 1598111 | * | 9/1981 |
| GB | 2151142 | | 7/1985 |
| JP | 59-85653 A | | 5/1984 |
| JP | 11-089937 | | 4/1999 |
| JP | 2000-283130 A | | 10/2000 |
| WO | WO 81/00668 | | 3/1981 |
| WO | WO 91/01689 | | 2/1991 |
| WO | WO 92/12690 | | 8/1992 |
| WO | WO 94/18881 | | 9/1994 |
| WO | WO 94/18893 | | 9/1994 |
| WO | WO 95/15715 A1 | | 6/1995 |
| WO | WO 96/14032 A1 | | 5/1996 |
| WO | WO 96/22735 | | 8/1996 |
| WO | WO 96/30072 A1 | | 10/1996 |
| WO | WO 97/18746 A2 | | 5/1997 |
| WO | WO 97/25927 A1 | | 7/1997 |
| WO | WO 97/26034 A1 | | 7/1997 |
| WO | WO 97/38748 A2 | | 10/1997 |
| WO | WO 97/39688 | | 10/1997 |
| WO | WO 97/48436 A2 | | 12/1997 |
| WO | WO 98/07375 | | 2/1998 |
| WO | WO 98/24372 | | 6/1998 |
| WO | WO 98/30153 | | 7/1998 |
| WO | WO 98/32382 | | 7/1998 |
| WO | WO 98/35638 | | 8/1998 |
| WO | WO 99/00059 | | 1/1999 |
| WO | WO 99/07354 | | 2/1999 |
| WO | WO 99/13777 A1 | | 3/1999 |
| WO | WO 99/66967 A1 | | 12/1999 |
| WO | WO 00/02489 | | 1/2000 |
| WO | WO 00/03651 A1 | | 1/2000 |
| WO | WO 00/03759 | | 1/2000 |
| WO | WO 00/12168 A1 | | 3/2000 |
| WO | WO 00/44313 A1 | | 8/2000 |
| WO | WO 00/59382 | | 10/2000 |
| WO | WO 00/60995 | | 10/2000 |
| WO | WO 01/00111 | | 1/2001 |
| WO | WO 01/00114 A1 | | 1/2001 |
| WO | WO 01/03651 A2 | | 1/2001 |
| WO | WO 01/26557 | | 4/2001 |
| WO | WO 01/26586 | | 4/2001 |
| WO | WO 01/26587 A1 | | 4/2001 |
| WO | WO 01/26588 A2 | | 4/2001 |
| WO | WO 01/26703 A1 | | 4/2001 |
| WO | WO 01/28432 | | 4/2001 |
| WO | WO 01/28455 | | 4/2001 |
| WO | WO 01/47438 A1 | | 7/2001 |
| WO | WO 01/49213 A2 | | 7/2001 |
| WO | WO 01/49213 A3 | | 7/2001 |
| WO | WO 01/50985 A1 | | 7/2001 |
| WO | WO 01/54618 | | 8/2001 |
| WO | WO 01/56512 A1 | | 8/2001 |
| WO | WO 01/66001 | | 9/2001 |
| WO | WO 01/70320 A1 | | 9/2001 |
| WO | WO 01/89440 A2 | | 11/2001 |
| WO | WO 01/95831 A2 | | 12/2001 |
| WO | WO 01/95832 A2 | | 12/2001 |
| WO | WO 01/97741 A2 | | 12/2001 |
| WO | WO 02/00099 A2 | | 1/2002 |
| WO | WO 02/01999 A2 | | 1/2002 |
| WO | WO 02/03892 | | 1/2002 |
| WO | WO 02/34167 A2 | | 5/2002 |
| WO | WO 02/34167 A3 | | 5/2002 |
| WO | WO 02/060352 A1 | | 8/2002 |
| WO | WO 02/062263 A2 | | 8/2002 |
| WO | WO 02/062270 A1 | | 8/2002 |
| WO | WO 02/062408 A2 | | 8/2002 |
| WO | WO 03/001893 | | 1/2003 |
| WO | WO 03/003930 A1 | | 1/2003 |
| WO | WO 03/020179 | | 3/2003 |
| WO | WO 03/028558 | | 4/2003 |
| WO | WO 03/037171 | | 5/2003 |
| WO | WO 03/047467 | | 6/2003 |
| WO | WO 03/049619 | | 6/2003 |
| WO | WO 03/073910 | | 9/2003 |
| WO | WO 03/073913 | | 9/2003 |
| WO | WO 03/105667 | | 12/2003 |
| WO | WO 2004/004607 | | 1/2004 |
| WO | WO 2004/012583 | | 2/2004 |
| WO | WO 2004/012789 A2 | | 2/2004 |
| WO | WO 2004/014282 A2 | | 2/2004 |
| WO | WO 2004/019811 | | 3/2004 |
| WO | WO 2004/030570 | | 4/2004 |
| WO | WO 2004/037317 | | 5/2004 |
| WO | WO 2004/045370 | | 6/2004 |
| WO | WO 2004/045378 | | 6/2004 |
| WO | WO 2004/045463 | | 6/2004 |
| WO | WO 2004/047679 | | 6/2004 |
| WO | WO 2004/062725 | | 7/2004 |
| WO | WO 2004/082523 | | 9/2004 |
| WO | WO 2004/082538 | | 9/2004 |
| WO | WO 2004/093730 | | 11/2004 |
| WO | WO 2004/112585 | | 12/2004 |
| WO | WO 2004/112651 | | 12/2004 |
| WO | WO 2005/002424 | | 1/2005 |
| WO | WO 2005/018507 | | 3/2005 |
| WO | WO 2005/027797 | | 3/2005 |
| WO | WO 2005/032421 | | 4/2005 |
| WO | WO 2005/062931 | | 7/2005 |
| WO | WO 2005/112792 | | 12/2005 |
| WO | WO 2006/105008 | | 10/2006 |
| WO | WO 2006/105009 | | 10/2006 |
| WO | WO 2006/115875 | | 11/2006 |
| WO | WO 2006/115876 | | 11/2006 |

OTHER PUBLICATIONS

Abe et al., "Updated: De Vega's annuloplasty for acquired tricuspid disease: Early and late results in 110 patients" Ann. Thorac. Surg. (1996) 62:1876-1877.

Agricola et al., "Mitral valve reserve in double orifice technique: an exercise echocardiographic study," Journal of Heart Valve Disease, (2002)11(5):637 643.

Alfieri, et al., "An effective technique to correct anterior mitral leaflet prolapse," J Card Surg, 1999; 14(6):468-470.

Alfieri et al., "Novel suture device for beating heart mitral leaflet approximation," Annals of Thoracic Surgery, (2002)74:1488 1493.

Alfieri et al., "The double orifice technique in mitral valve repair: a simple solution for complex problems," Journal of Thoracic Cardiovascular Surgery, (2001)122:674 681.

Alfieri et al., "The edge to edge technique," The European Association for Cardio-Thoracic Surgry 14th Annual Meeting, (2000) Oct. 7-11, Book of Proceedings.

Alfieri , "The edge-to-edge repair of the mitral valve," [Abstract] 6th Annual NewEra Cardiac Care: Innovation & Technology, Heart Surgery Forum, (2003) pp. 103.

Alvarez et al., "Repairing the degenerative mitral valve: Ten- to fifteen-year follow-up" J. Thorac. Cardiovasc. Surg. (1996) 112:238-247.

Arisi et al., "Mitral valve repair with Alfieri technique in mitral regurgitation of diverse etiology: early echocardiographic results," Circulation Supplement II, (2001) 104(17):3240.

Bach et al., "Early improvement in congestive heart failure after correction of secondary mitral regurgitation in end-stage cardiomyopathy," Am. Heart J., (1995) 129:1165-1170.

Bach et al., "Improvement following correction of secondary mitral regurgitation in end-stage cardiomyopathy with mitral annuloplasty" Am. J. Cardiol., (1996) 78:966-969.

Bailey, "Surgery of the Heart," Chapter 20, (1955) pp. 686-737.

Bernal et al., "The 'Valve Racket' : a new and different concept of atrioventricular valve repair," Eur. J. Cardio--thoracic Surgery 29:1026-29 (2006).

Bhudia, #58 Edge-to-edge mitral repair: a versatile mitral repair technique, 2003 STS Presentation, [Abstract Only].

Bhudia et al., "Edge-to-edge (Alfieri) mitral repair: results in diverse clinical settings," Ann Thorac Surg, 77: 1598-1606, (2004).

Bollling et al., "Surgery for acquired heart disease," (1995) 109:676-683.

Borghetti et al., "Preliminary observations on haemodynamics during physiological stress conditions following 'double-orifice' mitral valve repair," European Journal of Cardio-thoracic Surgery, Apr. 18, (2001) 20:262-269.

Castedo, "Edge-to-edge tricuspid repair for redeveloped valve incompetence after DeVega's annuloplasty," AnnThora Surg, (2003) 75;605-6.

Dec et al., "Idiopathic dilated cardiomyopathy," N. Engl. J. Med., (1994) 331:1564-1575.

Dottori et al., "Echocardiographic imaging of the Alfieri type mitral valve repair," Ital Heart J, (2001) 2(4):319-320.

Downing et al., "Beating heart mitral valve surgery: Preliminary model and methodology," Journal of Thoracic and Cardiovascular Surgery, (2002) 123(6):1141-1146.

Falk et al., "Computer-enhanced mitral valve surgery: toward a total endoscopic procedure," Seminars in thoracic and cardiovascular surgery, (1999) 11(3):224-249.

Filsoufi et al., "Restoring Optimal Surface of Coaptation With a Mini Leaflet Prosthesis: A New Surgical Concept for the Correction of Mitral Valve Prolapse," Int'l. Soc. for Minimally Invasive Cardiothoracic Surgery 1(4):186-87 (2006).

Frazier et al., #62 Early Clinical Experience With An Implantable, Intracardiac Circulatory Support Device: Operative Considerations and Physiologic Implications, 2003 STS Presentation, 1 page total. [Abstract Only].

Fucci et al., "Improved results with mitral valve repair using new surgical techniques" Eur. J. Cardiothorac Sug. (1995) 9:621-627 (Medline Record enclosed herewith.).

Fundaro et al., "Chordal plication and free edge remodeling for mitral anterior leaflet prolapse repair: 8-year follow-up," Annals of Thoracic Surgery, (2001) 72:1515-1519.

Garcia-Rinaldi et al., "Left ventricular volume reduction and reconstruction is ischemic cardiomyopathy," Journal of Cardiac Surgery, (1999) 14:199-210.

Gateliene , "Early and postoperative results of metal and tricuspid valve insufficiency surgical treatment using edge-to-edge central coaptation procedure," (2002) 38 Suppl 2:172-5.

Gatti et al., "The edge to edge technique as a trick to rescue an imperfect mitral valve repair," Eur J Cardiothorac Surg, (2002) 22(5):817 20.

Gillinov et al., "Is minimally invasive heart valve surgery a paradigm for the future?," Current Cardiology Reports, (1999) 1:318-322.

Gundry, "Facile mitral valve repair utilizing leaflet edge approximation: midterm results of the Alfieri figure of eight repair," Presented at the Meeting of The Western Thoracic Surgical Association, (1999).

Gupta et al., #61 Influence of Older Donor Grafts on Heart Transplant Survival: Lack of Recipient Effects, 2003 STS Presentation, [Abstract Only].

Ikeda et al., "Batista's operation with coronary artery bypass grafting and mitral valve plasty for ischemic dilated cardiomyopathy," The Japanese Journal of Thoracic and Cardiovascular Surgery, (2000) 48:746-749.

Izzat et al., "Early experience with partial left ventriculectomy in the Asia-Pacific Region," Annals of Thoracic Surgery, (1999) 67:1703-1707.

Källner et al., "Transaortic approach for the Alfieri Stitch," Ann Thorac Surg, 2001; 71:378-380.

Kameda et al., "Annuloplasty for severe mitral regurgitation due to dilated cardiomyopathy," Am. Thorac. Surg, (1996) 61:1829-1832.

Kavarna et al., "Transaortic repair of mitral regurgitation," Presented at the third annual New Era Cardiac Care conference, San Diego, CA, (2000) Jan. 13-16, http://www.hsforum.com/vol3/issue1/2000-2389print.html.

Kaza et al., "Ventricular reconstruction results in improved left ventricular function and amelioration of mitral insufficiency," Annals of Surgery, (2002) 235(6):828 832.

Khan et al., "Blade atrial septostomy: Experience with the first 50 procedures" Cathet. Cardiovasc. Diagn, (1991) 23:257-262.

Kherani et al., "Edge-to-edge mitral valve repair: the Columbia Presbyterian experience," Ann Thorac Surg, 2004; 78: 73-76.

Konertz et al., "Results after partial left ventriculectomy in a European heart failure population," J. Cardiac Surg, 1999; 14(2):129-135.

Kron et al., "Surgical relocation of the posterior papillary muscle in chronic ischemic mitral regurgitation," Annals. of Thoracic Surgery, (2002)74:600 601.

Krüger et al, "Edge to edge technique in complex mitral valve repair," Thorac Cardiovasc Surg, 2000, Thema: Poster, http://www.thieme.de/thoracic/abstracts/abstracts/p_73.html.

Langer et al., "Posterior mitral leaflet extensions: An adjunctive repair option for ischemic mitral regurgitation?," J. Thorac. Cardiovasc. Surf. 131:868-77 (2006).

Lorusso e al., "Double-Orifice" technique to repair extensive mitral valve excision following acute endocarditis, J Card Surg, 1998; 13:24-26.

Lorusso et al., "The double-orifice technique for mitral valve construction: predictors of postoperative outcome," Eur J. Cardiothorac Surg, May 23, 2001; 20(3):583-589.

Maisano et al., "The double orifice repair for Barlow Disease: a simple solution for a complex repair," Supplement I Circulation, 1999; 100(18):1-94.

Maisano et al., "The double orifice technique as a standardized approach to treat mitral regurgitation due to severe myxomatous disease: surgical technique," Eur J. Cardiothoracic Surg., Jan 18, 2000; 17:201-215.

Maisano et al., "The hemodynamic effects of double-orifice valve repair for mitral regurgitation: a 3D computational model," European Journal of Cardio-thoracic Surgery, 1999; 15:419-425.

Maisano et al., "Valve repair for traumatic tricuspid regurgitation," Eur J. Cardio-Thorac Surg, 1996; 10:867-873.

Maisano et al., "The edge-to-edge technique: A simplified method to correct mitral insufficiency" Eur. J. Cardiothorac. Surg., (1998) 13:240-246.

Mantovani et al., "Edge-to-edge repair of congenital familiar tricuspid regurgitation: case report," J. Heart Valve Dis, Sep. 2000; 9 (5):641-643.

McCarthy et al. "Tricuspid valve repair with the Cosgrove-Edwards annuloplasty system" Am. Thorac. Surg., (1997) 64:267-268.

McCarthy et al., "Partial left ventriculectomy and mitral valve repair for end-stage congestive heart failure," Eur J. Cardio-thoracic Surgery, 1998; 13:337-343.

Moainie et al., Correction of traumatic tricuspid regurgitation using the double orifice technique, Annals of Thoracic Surgery, (2002) 73:963 965.

Morales et al., "Development of an off bypass mitral valve repair," The Heart Surgery Forum #1999-4963, (1999) 2(2):115-120.

Nakanishi et al., "Early outcome with the Alfieri mitral valve repair," J Cardiol, May 2001; 37(5):263-266, (Abstract in English; Article in Japanese.).

Nielsen et al., "The edge-to-edge mitral repair: tension on the approximating suture and leaflet deformation during acute ischemic mitral regurgitation in the ovine heart, " Circulation, 2001;104 [ suppl 1]:1-29-1-35.

Noera et al., "Tricuspid Valve Incompetence Caused by Nonpenetrating Thoracic Trauma", Annals of Thoracic Surgery, 1991, 51 (2), 320-322.

Osawa et al., "Partial left ventriculectomy in a 3 year old boy with dilated cardiomyopathy," Japanese Journal of Thoracic and Cardiovascular Surg, Sep. 2000, 48(9):590-593.

Park et al., "Clinical use of a blade atrial septostomy" Circulation (1978) 58:600-608.

Patel et al., #57 Epicardial Atrial Defibrillation: Novel Treatment of Postoperative Atrial Fibrillation, 2003 STS Presentation, [Abstract Only].

Privitera et al., "Mitral Valve Repair: Clinical Outcome and Pathology; Circulation," (2002) 106:173.

Redaelli et al., A computational study of the hemodynamics after 'edge-to-edge' mitral valve repair, Journal of Biomechanical Engineering, (2001) 123:565-570.

Reul et al., "Mital valve reconstruction for mitral insufficiency," Progress in Cardiovascular Diseases, (1997) vol. XXXIX, No. 6, pp. 567-599.

Ricchi et al., "Linear segmental annuloplasty for mitral valve repair" Ann. Thorac. Surg., (1997) 63:1805-1806.

Robicsek et al., #60 The Bicuspid Aortic Valve: How Does It Function? Why Does It Fail?, 2003 STS Presentation, [Abstract Only].

Tager et al., "Long-term follow-up of Rheumatic patients undergoing left-sided valve replacement with tricuspid annuloplasty—Validity of preoperative echocardiographic criteria in the decision to perform tricuspid annulopasty" Am. J. Cardiol., (1998) 81:1013-1016.

Tamura et al., Edge to edge repair for mitral regurgitation in a patient with chronic hemodialysis: report of a case, Kyobu Geka, (2001) 54(9):788-790.

Tibayan et al., #59 Annular Geometric Remodeling in Chronic Ischemic Mitral Regurgitation, 2003 STS Presentation, [Abstract Only].

Timek et al., "Edge-to-edge mitral repair: gradients and three-dimensional annular dynamics in vivo during inotropic stimulation," Eur J. of Cardiothoracic Surg., Jan. 9, 2001; 19:431-437.

Timek, "Edge-to-edge mitral valve repair without annuloplasty ring in acute ischemic mitral regurgitation," [Abstract] Clinical Science, Abstracts from Scientific Sessions, (2002) II-461.

Totaro et al., "Mitral valve repair for isolated prolapse of the anterior leaflet: an 11 year follow-up," Eur J. Cardio-Thoracic Surg, 1999; 15:119-126.

Uchida et al., "Percutaneous cardiomyotomy and valvultomy with angioscopic guidance," Am. Heart J., (1991) 121:1221-1224.

Umana et al., "'Bow-tie' mitral valve repair successfully addresses subvalvular dysfunction in ischemic mitral regurgitation," (1997) Surgical Forum pp. 279-280.

Umana, "'Bow-Tie' mitral valve repair: an adjuvant technique for ischemic mitral regurgitation," AnnThora Surg, (1998) 66:1640-6.

Votta et al., "3 D computational analysis of the stress distribution on the leaflets after edge to edge repair of mitral regurgitation," Journal of Heart Valve Disease, (2002)11:810 822.

* cited by examiner

SURGICAL DEVICE FOR CONNECTING SOFT TISSUE

CROSS-REFERENCES TO RELATED APPLICATIONS

The present application is a continuation of U.S. patent application Ser. No. 11/354,612 now U.S. Pat. No. 7,682,369, filed on Feb. 14, 2006, which is a continuation U.S. patent application Ser. No. 10/877,279 now U.S. Pat. No. 7,288,097, filed on Jun. 24, 2004, which is a divisional of U.S. patent application Ser. No. 10/202,599 now U.S. Pat. No. 6,770,083, filed Jul. 24, 2002, which is a divisional of U.S. patent application Ser. No. 09/523,018 now U.S. Pat. No. 6,461,366, filed Mar. 10, 2000, which is a continuation of PCT/FR98/01960, which designated the United States, filed Sep. 12, 1997, the full disclosure of which is incorporated herein by reference.

BACKGROUND OF THE INVENTION

This invention provides a surgical device allowing the percutaneous connection of two soft tissue areas that are ordinarily separate. This device is particularly intended for reconstruction of heart valves, especially the mitral valve, and for the treatment of any malformation of a heart septum.

In a condition known as mitral insufficiency, the mitral valve does not completely shut, and does not prevent the back-flow of blood to the left atrium from the left ventricle. Surgical repair is then necessary. In a current procedure, a sternotomy is performed. The patient is then placed under extra-corporal blood circulation while the heart is stopped, and the heart chambers are opened to gain access to the mitral valve, usually through the left atrium. Once the mitral valve is accessed, repair procedures include annuloplasty and, more recently, suturing of the free edge of the anterior leaflet to the free edge of the back leaflet where the mitral insufficiency occurs.

These procedures are complicated and require general anesthesia, sternotomy and extra-corporal blood circulation. They also require high doses of anti-coagulant therapy adding to the operative risk of a myocardial infarction and hemorrhage.

SUMMARY OF THE INVENTION

The methods of the present invention are performed percutaneously, diminishing considerably these risks. A surgical device allows the connection of two zones of soft tissue that are usually separate. In a particular embodiment, a connection is formed between a free edge area of an anterior mitral leaflet and a free edge area of a back mitral leaflet. Suitable surgical devices for performing tissue connection are described for example in EP 558 031 and WO 94/18893, and may comprise:

(a) a tube which may be inserted percutaneously until its distal extremity reaches the area around the tissues to be connected; and (b) two elongated elements inside that tube, each of which comprises a distal extremity having a device that grasps one of the two tissues to be connected;

(c) wherein the distal extremities of these elongated elements may be opened and closed in order to permit introduction into the desired area, allow the procedure.

Particular devices according to the present invention may further comprise:

(a) a grasping element, optionally having two parts for capturing each of the tissues to be connected, wherein the grasping or hooking element effects the connection of the two zones of tissue when brought close thereto by shifting of the portions of distal extremities to a position where they meet;

(b) a rod connected to each of the grasping or hooking elements and operated from the proximal end of the tube in order to axially shift the elongated element, wherein the rod can be separated from the grasping or hooking element upon pulling beyond a given threshold; and (c) a wedge inside the tube, allowing the axial immobilization of each grasping or hooking element while pulling on them.

The rod positions the insertion of the hooking element up to the level of the tissue edges to be connected. The rod also engages the hooking element against the wedge in order to open the two hooking parts.

According to the present invention, the device may be used to remotely grasp through a percutaneous passage, to draw together, and to connect the two zones of tissue by a simple external manipulation.

Preferably, the tube, the elongated elements, and the rod are flexible enough to be inserted percutaneously and through a patient's vasculature for the treatment of the leaflets of a cardiac valve, in particular the mitral valve. Each of the elongated elements is made out of an elastically flexible material, and one of these elongated elements diverges from the longitudinal axis of the other. The two elongated elements can move axially in relation to the tube between (a) a retracted position within the tube where the ends of the elongated elements are flexibly bent and closed together, and (b) a position where the ends of the elongated elements spring open and diverge from each other in a way that permits those ends to capture the soft tissues in order to grasp them.

The elongated elements may be deployed to allow their distal extremities to grasp the tissue areas or may be retracted in order to make the insertion, shifting or removal of the apparatus easier. Each elongated element may comprise a rod made of elastic material, with a curved distal extremity and/or a harpoon shape, and a sheath able to slide axially in a forward position to cover the distal extremity and slide back to uncover it.

According to a variation, each elongated element can be composed of a tube linked to a system that contracts its internal volume in order to grasp the corresponding tissue area, and expands to release the tissue with no lesion. In this case, the wide-mouthed shape of the elongated element's distal extremity will insure a large enough grasping surface.

Preferably, the device includes two hooking elements. One is operated on the distal side of the tissues, and the other, to be operated on the proximal side of the tissues, is situated between the first hooking element and the wedge element. This way the two hooking elements can be operated on both sides of the tissues and can be pressed together for a perfect attachment of those tissues.

BRIEF DESCRIPTION OF THE DRAWINGS

For greater clarity, the invention is described again in reference to the enclosed Figures representing two unrestricted examples of the invention in its optimal capacity.

DESCRIPTION OF THE SPECIFIC EMBODIMENTS

Figure 1:
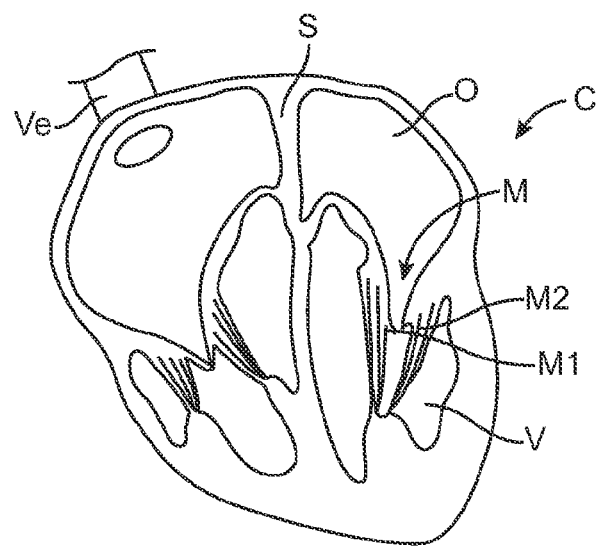
FIG. 1 shows a longitudinal section of a heart with a mitral valve that does not shut properly and has to be treated with this device.
Figure 2:
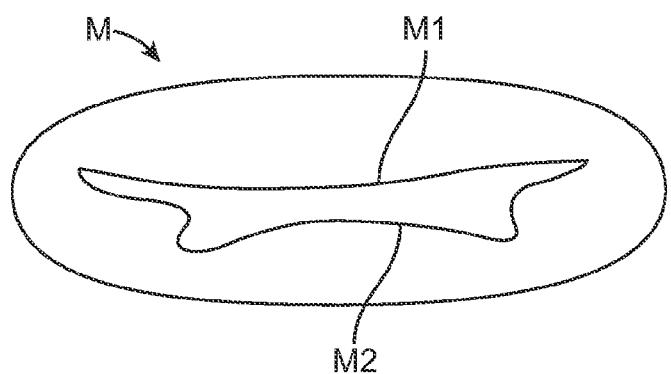
FIG. 2 shows the mitral valve before treatment.
Figure 3:
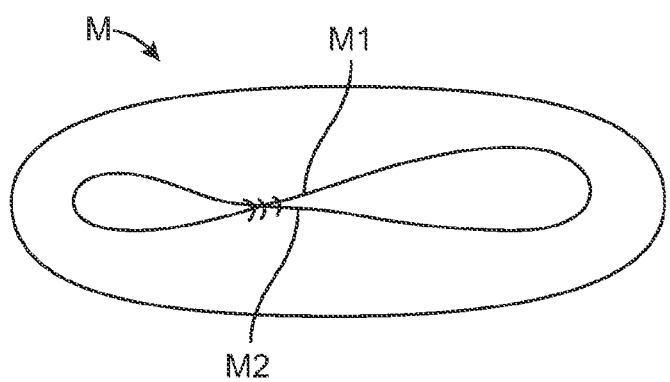
FIG. 3 shows a mitral valve similar to FIG. 2 after treatment by suture according to the usual procedure.

FIG. 1 shows a heart C with a mitral valve M having poorly opposed leaflets (M1, M2). Thus, the valve M does not shut tightly and no longer performs its back-flow function between the left atrium O and the left ventricle V. According to conventional procedures, after sternotomy, the patient is placed under extra-corporal blood circulation. The heart is stopped and the heart chambers are opened to directly reach to the valve M and stitch together the free opposite edges of both leaflets (M1, M2) as shown on FIGS. 2 and 3. Connecting leaflets M1 to M2 restores a good attachment between them and restores the imperviousness of valve M.

Figure 4:
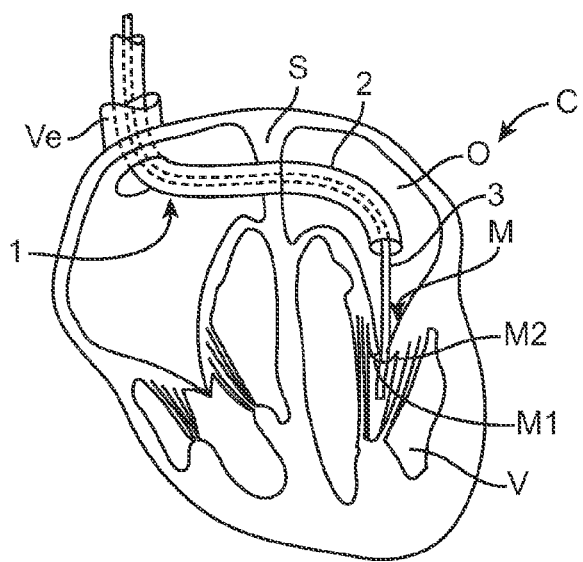
FIG. 4 is a view similar to that of FIG. 1, with the device of the present invention inserted into a heart.
Figure 5:
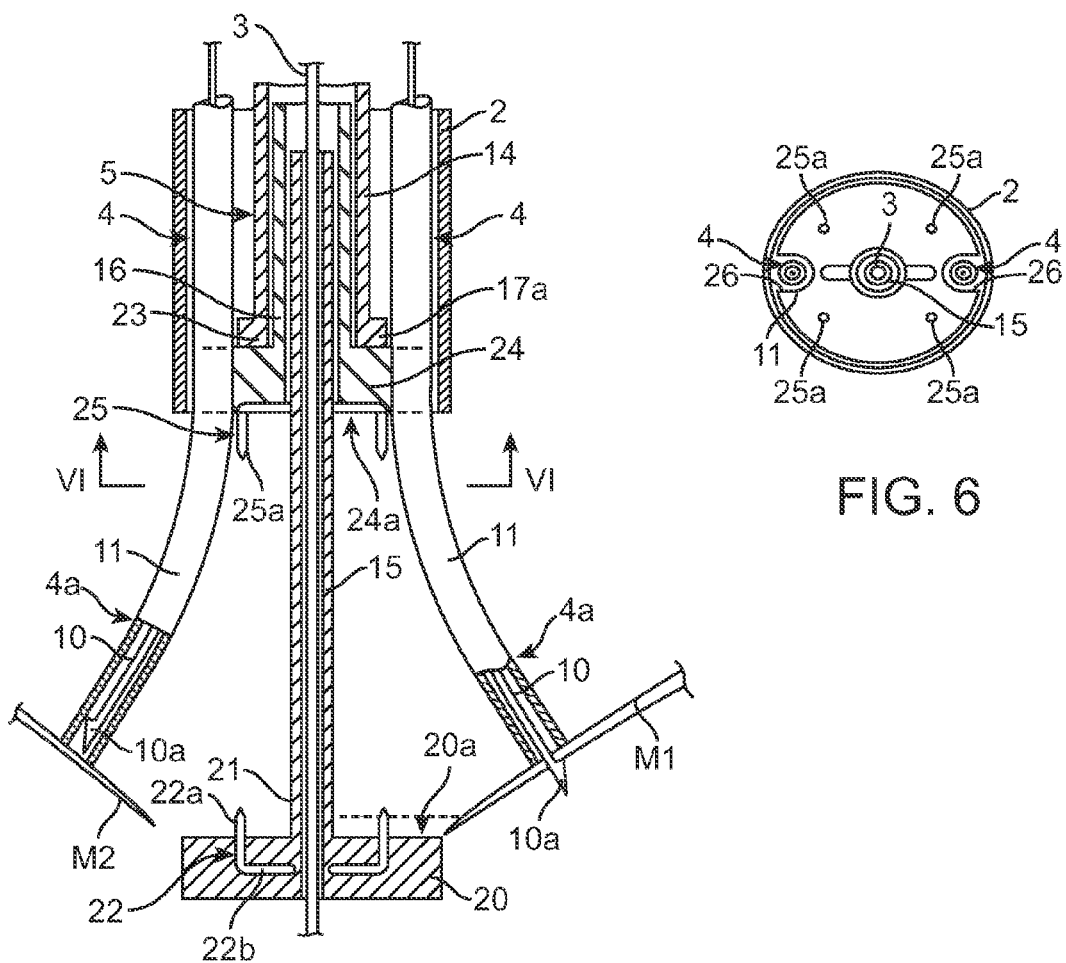
FIG. 5 is an enlarged view of a longitudinal section of the distal extremity of the device.

FIGS. 4 to 5 show a device (1) according to the present invention which enables the percutaneous connection of leaflet M1 to leaflet M2. This device (1) comprises an external tube (2), guidewire (3), two elongated elements (4), and a clipping system (5). The apparatus is sufficiently flexible to be percutaneously inserted into the heart C, through the patient's vascular, e.g., the Vena Cava Ve and the intra-atrial septum S.

Guidewire (3) is inserted through valve M and so the distal extremity of external tube (2) is located in the left atrium O, with its distal opening facing mitral valve M.

Figure 7:
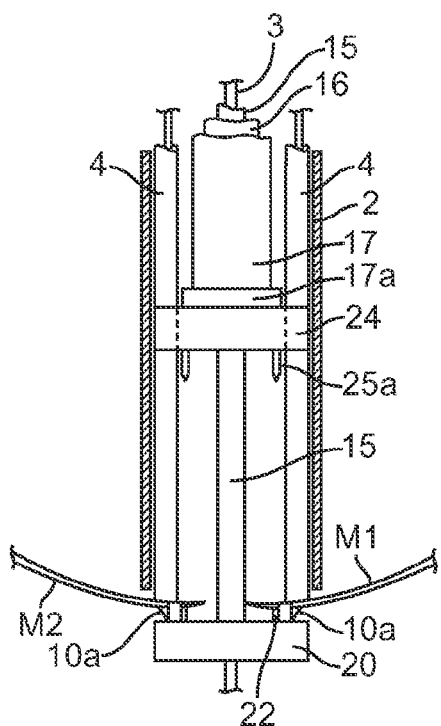
FIG. 7 and FIG. 8 are similar views to FIG. 5 at different stages of the procedure.
Figure 8:
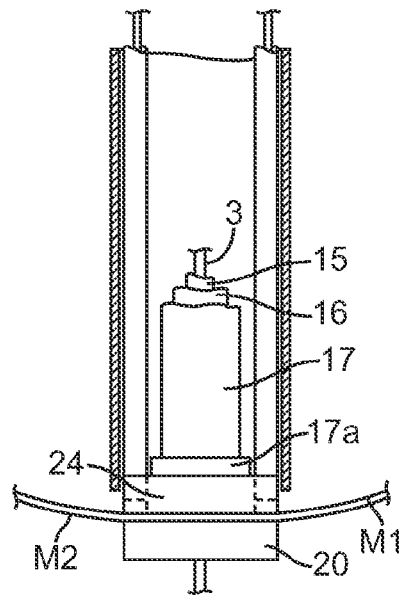

Each of the elongated elements (4) has a distal extremity (4a) that is normally curved to diverge outwardly. A rod (10) is made out of a relatively rigid but still elastic material, more particularly in metal, with a sheath (11) of synthetic material. The distal extremity (10a) of the rod (10) is sharp and more or less harpoon-shaped. The sheath (11) fits on the rod (10) and can slide axially to a forward position (as shown on left side of FIG. 5) in order to cover the distal extremity of the rod, and can slide back (as shown on the right side of FIG. 5) in order to uncover that same distal extremity (10a). The elongated elements (4) extend from the end of the tube (2). Because of this, they can be shifted axially in relation to the tube (2) between a retracted position where the extremities (10a) close together (FIGS. 7 and 8) and an extended position where these same extremities (10a) diverge from each other (FIG. 5). The clipping system (5) comprises three concentric tubular rods (15, 16, 17) that can be slidably introduced over the guidewire (3). Each rod can also slide axially in relation to the others. The internal rod (15) is linked to a disk (20) through a frangible area (21). The rod and disk (15 and 20) are made of molded synthetic material. The disk (20) is axially pierced in order to let the guidewire (3) pass through, and carries a clip (22). Side prongs (22a) of that clip extend from the proximal face (20a) of the disk (20). A central portion (22b) of the clip (22) having a central ring for receiving the guidewire (3) is embedded into the material of the disk (24).

Figure 6:
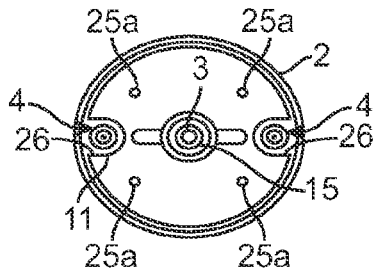
FIG. 6 shows a view of this distal extremity according to the line VI-VI of FIG. 5.

The intermediate rod (16) is also connected by a frangible area (23) to a disk (24) with two clips (25). Side prongs (25a) of these clips extend from the distal face (24a) of this disk (24), and central portions of the prongs are embedded into the material of the disk (24). On each side, the disk (24) has two diametrically opposed notches (26, FIG. 6) to allow the passage of the elongated elements (4). The external rod (17) has an expanded distal extremity (17a) which engages the proximal face of the disk (24). Each of these rods (15, 16, 17) can be extended beyond the proximal extremity of tube (2) so they can be shifted by the operator.

A handle or other structure for manipulating the rods (15, 16, 17) will usually be provided at a proximal end of the device. The handle will permit deployment rod (15) while rod (17) is held in a desired position in relation to tube (2), and then deployment rod (16), while rod (17) is also held in the desired position in relation to tube (2).

In practice, under X-ray or echography control, the guidewire (3) is first inserted through Vena Cava Ve, the intra-atrial septum S, and mitral valve M. Then tube (2) and its internal parts are inserted into the Vena Cava Ve and through the septum S until the distal extremity of tube (2) is directed at mitral valve M (FIG. 4). At this stage, disk (20) should be held at the opening of tube 2 (FIG. 5), while elongate elements (4) are retracted so that their distal extremities are retracted into slots (26).

When the distal extremity of tube (2) is in the proper position, rod (15) is shifted to advance disk (20) beyond leaflets M1 and M2 and into the left ventricle V. Elongate elements (4) are then advanced to their extended positions, as shown in FIG. 5. As the elongate elements (4) are advanced, their distal extremities diverge. After the elements (4) are advanced, distal extremities (10a) of rods (10) are positioned close to leaflets (M1, M2). The sheaths (11) of elements (4) are then retracted in relation to the rods (10) in order to uncover the extremities (10a), each of which can then pierce and capture the adjacent leaflet M1 or M2. Tube (2) is then advanced over the elongate elements (4), drawing the distal extremities (4a) closer, as shown on FIG. 7. This action draws the free edges of leaflets M1 and M2 together.

Figure 9:
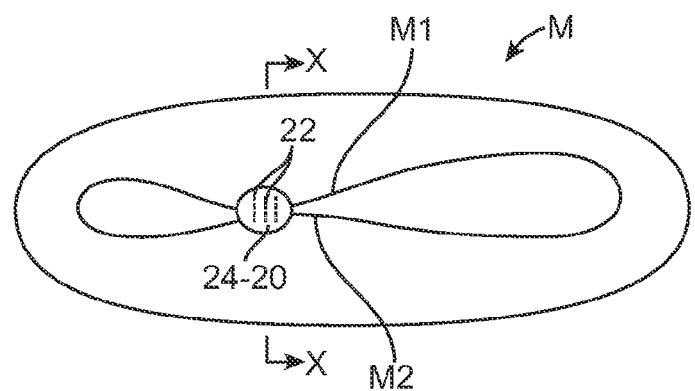
FIG. 9 is a similar view to FIG. 2 of the mitral valve after treatment with the device.
Figure 10:
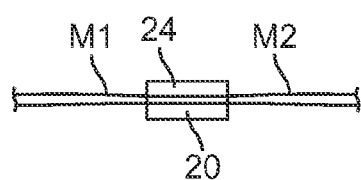
FIG. 10 is a view of this valve according to line X-X of FIG. 9.

Rod (17) is advanced distally in relation to tube (2), and rod (15) is pulled proximally in relation to tube (2) in order to insert the prongs (22a and 25a) of clips (22 and 25) into the leaflets M1 and M2. The tension on rod (15) forces the prongs (22a and 25a) against the opposed walls (20a, 24a) of the disks (20, 24) and breaks frangible area (21). This break gives the prongs of the clips enough freedom of movement to ensure a good connection between leaflets M1 and M2. The sheaths (11) are then advanced distally in relation to the rods (10) to engage leaflets (M1, M2). This facilitates the extremities (10a) of the rods from the leaflets (M1, M2). Rod (16) is then pulled while holding rod (17) in position to break frangible area (25). Leaflets (M1, M2) have thus been clipped to each other by their free edges, as shown in FIGS. 9 and 10.

Figure 11:
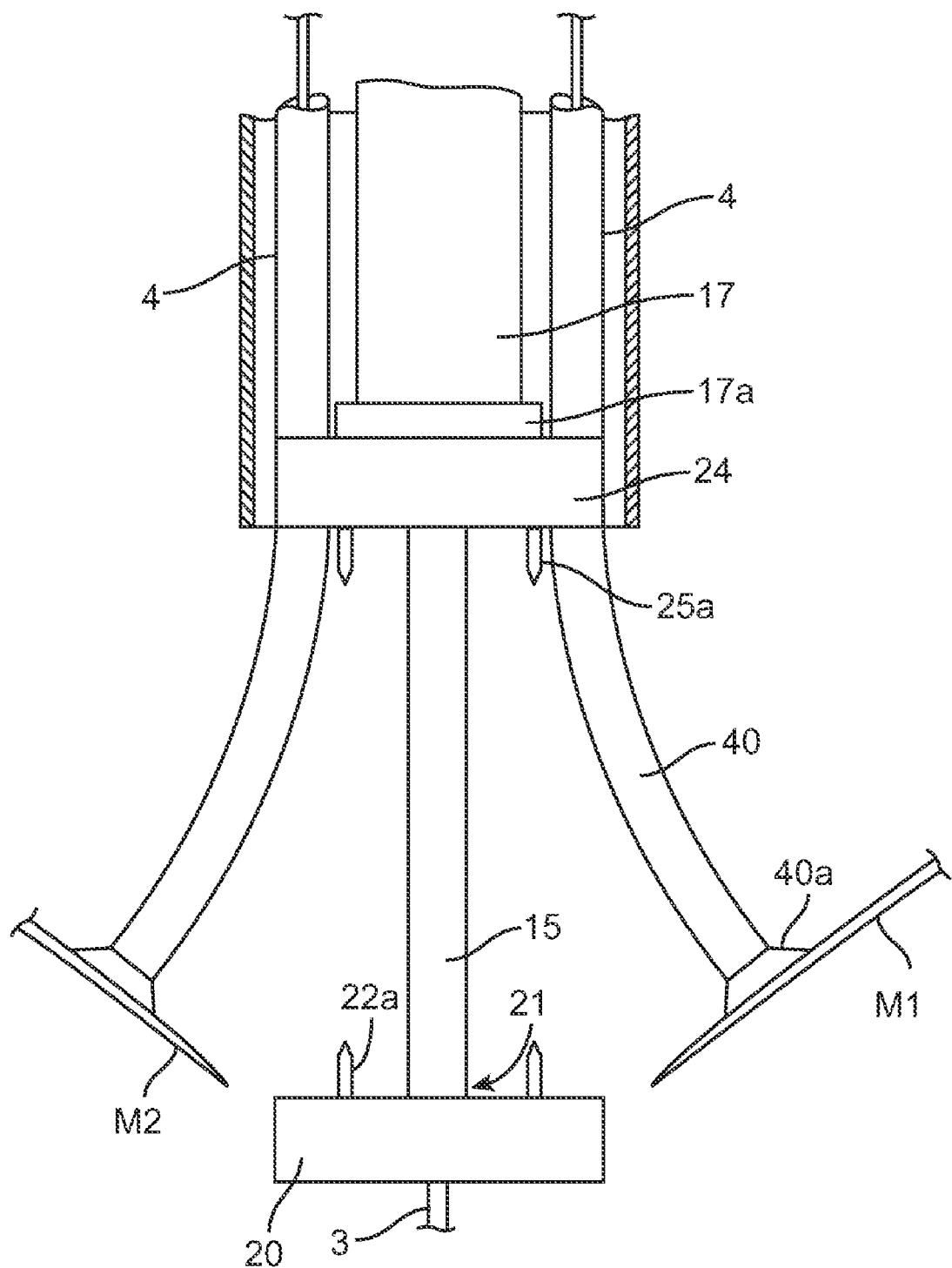
FIG. 11 illustrates an alternative embodiment of the device of the present invention.

FIG. 11 shows a variation of the apparatus where rods (10) and sheaths (11) have been replaced by two catheters (40) having trumpeted distal extremities (40a). These catheters (40) project beyond the proximal end of tube (2) and may be attached to syringes that permit the creation of negative pressure. The grasping or releasing of leaflets (M1, M2) is then achieved by controlling the internal pressure within catheters (40). The trumpeted ends (40a) ensure a sufficient grip on leaflets (M1, M2). Those ends (40a) are preferably sufficiently flexible enough to bend slightly when they are drawn between the wall of tube (2) and two lateral slots (26) of disk (20). The other parts of this alternative device are the same as already described and bear the same record numbers.

It goes without saying that the invention is not limited to the above example and is opened to different variations. For instance, the unstressed shape of the extremities (10a) that hook the tissues could be of a curved J which is straightened when drawn into the sheaths (11). The elongated parts (4) and the connecting system could also be placed in separate tubes. The device (1) could be inserted arterially as well as veinously.

What is claimed is:

1. A system for repairing a cardiac valve, said system comprising:
 a tube suitable for introduction through a patient's vasculature and into a chamber of a heart;
 a clipping system comprising a first element adapted to be brought up beneath a pair of valve leaflets from the ventricular side and a second element adapted to be brought down over the pair of valve leaflets from the atrial side, wherein the first element engages the ventricular side of both leaflets and the second element engages the atrial side of both the leaflets to capture both leaflets therebetween and wherein the first and second elements may be left to attach the free edges of the leaflets together; and
 a pair of elongate elements each having a distal extremity for grasping or releasing a valve leaflet, the pair of elongate elements in fluid communication with a vacuum source and extensible from a distal end of the tube, wherein the valve leaflets are grasped when vacuum is applied to the elongate elements.

2. The system of claim 1, wherein the tube further comprises a lumen therethrough, and wherein the clipping system and the pair of elongate arms may be retracted into, and advanced from the lumen.

3. The system of claim 1, wherein the first pair of elements comprise a first pair of prongs, and the second pair of elements comprise a second pair of prongs.

4. The system of claim 3, wherein the first pair of prongs project toward the second pair of prongs.

5. The system of claim 4, wherein the first pair and the second pair of prongs penetrate the pair of valve leaflets.

6. The system of claim 1, wherein the pair of elongate elements are spring-biased to diverge outwardly when advanced distally from the tube.

7. The system of claim 1, wherein the distal extremity of each of the pair of elongate elements comprise a trumpeted distal extremity.

* * * * *